United States Patent
Schiemann et al.

(10) Patent No.: US 7,291,633 B2
(45) Date of Patent: Nov. 6, 2007

(54) 6H-OXAZOLO[4,5-E]INDOLE DERIVATIVES AS NICOTINIC ACETYLCHOLINE RECEPTOR LIGANDS AND/OR SEROTONERGIC LIGANDS

(75) Inventors: Kai Schiemann, Darmstadt (DE); Henning Böttcher, Darmstadt (DE); Joachim Leibrock, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 394 days.

(21) Appl. No.: 10/476,306

(22) PCT Filed: Apr. 5, 2002

(86) PCT No.: PCT/EP02/03784

§ 371 (c)(1),
(2), (4) Date: Oct. 29, 2003

(87) PCT Pub. No.: WO02/088139

PCT Pub. Date: Nov. 7, 2002

(65) Prior Publication Data

US 2005/0101649 A1    May 12, 2005

(30) Foreign Application Priority Data

Apr. 30, 2001  (DE) ................................ 101 21 217

(51) Int. Cl.
*A61K 31/424*   (2006.01)
*A61K 31/445*   (2006.01)
*A61K 31/5377*  (2006.01)
*C07D 401/14*   (2006.01)
*C07D 413/14*   (2006.01)
*C07D 498/02*   (2006.01)

(52) U.S. Cl. ...................... 514/323; 544/106; 544/142; 544/358; 544/367; 546/184; 546/192; 546/196; 546/201; 548/215; 548/217; 548/218; 514/231.5; 514/252.12; 514/315; 514/375

(58) Field of Classification Search ................ 548/215, 548/217, 218; 514/375, 323, 315, 231.5; 544/142, 367; 546/184, 201
See application file for complete search history.

(56) References Cited

U.S. PATENT DOCUMENTS

| 5,650,427 A | 7/1997 | Wikstrom et al. |
| 6,255,306 B1 | 7/2001 | Macor |
| 6,548,530 B1 * | 4/2003 | Boger .................... 514/410 |

FOREIGN PATENT DOCUMENTS

DE  10045112 A  3/2002

| WO | WO 9111435 A | 8/1991 |
| WO | WO 9213856 A | 8/1992 |
| WO | WO 9603400 A | 2/1996 |
| WO | WO 9946259 A | 9/1999 |

OTHER PUBLICATIONS

Boger et al (1997): STN International HCAPLUS database, Columbus (Ohio), accession No. 1997:366275.*
Grinev et al (1981): STN International HCAPLUS database, Columbus (OH), accession No. 1981:442808.*
Boger, Dale L. et al: "CBI-CDPBO1 and CBI-CDPBI1: CC-1065 analogs containing deep-seated modifications in the DNA binding subunit" Bioorg. Med. Chem. 1995, 3(6), 761-75.
Makosza, Mieczyslaw et al: "Synthesis of 1, 3, 4, 5-tetrahydropyrrolo '4, 3, 2-del quinoli nes via the vicarious nucleophilic substitution of hydrogen" TETRAHEDRON (1995), 51(26), 7263-76.
John E Macor et al : "1-(2-Aminomethyl) -3-methyl-8,9-dihydropyrane '3, 2-eindole:A Ratationalyy Restricted Phenolic Analog of the Neurotransmitter Serotonin and Agonist Selective for Serotonin (5-HT2-Type) Receptors" Journal of Medicinal Chemistry, American Chemical Society. Washington,US, vol. 35, No. 20, Oct. 2, 1992, pp. 3625-3632.

* cited by examiner

*Primary Examiner*—Golam M. M. Shameem
(74) *Attorney, Agent, or Firm*—Millen, White, Zelano & Branigan, P.C.

(57) ABSTRACT

Compounds of the formula I in which $R^1$, $R^2$, $R^3$ and $R^4$ are as defined in claim 1, are ligands of the nicotinic acetylcholine receptor and/or serotonergic ligands and are suitable for the prophylaxis or treatment of psychoses, schizophrenia, depression, anxiety states, dementia, in particular Alzheimer's disease and Lewy bodies dementia, neurodegenerative disorders, Parkinson's disease, amyotrophic lateral sclerosis, Huntington's disease, Tourette's syndrome, learning and memory restrictions, bulimia anorexia nervosa or other eating disorders, compulsvie behaviour, premenstrual syndrome, age-induced memory impairment, amelioration of withdrawal symptoms in nicotine dependence, strokes or brain damage by toxic compounds, and for the treatment of disorders which are characterised by an excess of circulating serotonin or by serotonergic hyperactivity

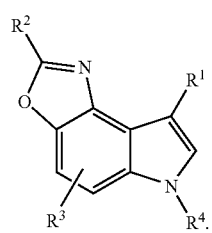

(I)

7 Claims, No Drawings

6H-OXAZOLO[4,5-E]INDOLE DERIVATIVES AS NICOTINIC ACETYLCHOLINE RECEPTOR LIGANDS AND/OR SEROTONERGIC LIGANDS

The invention relates to 6H-oxazolo[4,5-e]indole derivatives of the formula I

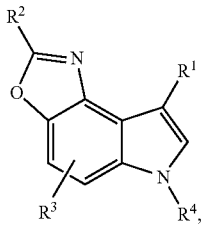

in which
$R^1$ is H or $Het^1$,
$R^2$ is H, A, cycloalkyl, —$(CH_2)_p$—$N(R^5)_2$, —$(CH_2)_p$—$OR^5$, —$(CH_2)_n$—Ar or —$(CH_2)_n$-Het,
$R^3$ is H, Hal, OH, OA or O—$(CH_2)_n$—Ar,
$R^4$ is H, A or —$(CH_2)_n$—Ar,
$R^5$ is H or A,
A is a linear or branched alkyl group having from 1 to 10 carbon atoms,
Ar is phenyl, naphthyl or biphenyl, each of which is unsubstituted or monosubstituted or polysubstituted by Hal, A, $OR^5$, $N(R^5)_2$, $NO_2$, CN, $COOR^5$, $CON(R^5)_2$, $NR^5COR^5$, $NR^5CON(R^5)_2$, $NR^5SO_2A$, $COR^5$, $SO_2NR^5$ or $S(O)_mA$,
cycloalkyl is cycloalkyl having from 3 to 10 carbon atoms,
Hal is F, Cl, Br or I,
Het is a saturated, unsaturated or aromatic monocyclic or bicyclic heterocyclic radical having from 5 to 10 ring members, which may contain from 1 to 4 N and/or from 1 to 4 S and/or from 1 to 4 O atoms, and in which the heterocyclic radical may be monosubstituted, disubstituted or trisubstituted by Hal, A, —$[C(R^5)_2]_o$—Ar, —$[C(R^5)_2]_o$-cycloalkyl, $OR^5$, $N(R^5)_2$, $NO_2$, CN, $COOR^5$, $CON(R^5)_2$, $NR^5COA$, $NR^5CON(R^5)_2$, $NR^5SO_2A$, $COR^5$, $SO_2NR^5$ or $S(O)_mA$ and/or carbonyl oxygen,
$Het^1$ is a saturated, unsaturated or aromatic monocyclic, bicyclic or tricyclic heterocyclic radical having from 5 to 10 ring members which contains at least 1 N atom and in which the heterocyclic radical may be monosubstituted, disubstituted or trisubstituted by Hal, A, $OR^5$, $N(R^5)_2$, $NO_2$, CN and/or carbonyl oxygen,
n is 0, 1, 2, 3, 4, 5, 6, 7 or 8,
m is 1 or 2,
o is 0, 1, 2, 3 or 4,
p is 1, 2, 3, 4, 5, 6, 7 or 8, and their physiologically acceptable salts and solvates.

The invention had the object of finding novel compounds having valuable properties, in particular those which can be used for the preparation of medicaments.

It has been found that the compounds of the formula I and their physiologically acceptable salts and solvates are well tolerated and have valuable pharmacological properties since they act on the central nervous system. The compounds are nicotinic acetylcholine receptor ligands and/or serotonergic ligands.

Of the well-characterised class of acetylcholine receptors, some members have been implicated in certain disorders of the central nervous system. Known active ingredients which are able to interact with the acetylcholine receptor class are, for example, pilocarpine, nicotine, lobeline and epibatidine.

These nicotinic acetylcholine receptors can be divided into two main classes, depending on the sites at which they occur.

The first class comprises the neuromuscular receptors. These are subdivided into $(\alpha_1\alpha_1\beta\epsilon\delta)$ and $(\alpha_1\alpha_1\beta\gamma\delta)$ receptors. The second class comprises the neuronal nicotinic acetylcholine receptors, which are found in the ganglia. In these, a distinction is made between the $(\beta_2-\beta_5)$ receptors and the $(\alpha_2-\alpha_9)$ receptors, in this respect see also "Basic Neurochemistry", Ed. Siegel et al., Raven Press, New York, 1993.

The substances of the formula I are capable of interacting with each of these receptors. The substances of the formula I interact particularly well with the nicotinic $\alpha_7$ receptor.

In-vitro evidence of the interaction with the nicotinic $\alpha_7$ receptor can be obtained, for example, analogously to J. M. Ward et al., Febuary 1990, 270, 45-48 or D. R. E. Macallan, Febuary 1998, 226, 357-363.

Further in-vitro tests for nicotinic receptors are described in F. E. D'Amour et al., Manual for Laboratory Work in Mammalian Physiology, 3rd Ed., The University of Chicago Press (1965), W. Sihver et al., Neuroscience 1998, 85, 1121-1133 or B. Latli et al., J. Med. Chem. 1999, 42, 2227-2234.

Serotonergic ligands are ligands of the 5-$HT_3$ receptor and/or of the 5-$HT_6$ receptor.

5-$HT_6$ receptors form a sub-family of 5-HT receptors. The neurotransmitter 5-hydroxytryptamine (5-HT), also known as serotonin, is an important regulatory neurotransmitter in the brain whose actions are supported by a family of receptors, which, as far as we know today, contain 13 G-protein-coupled receptors and an ion channel.

The greatest density of serotonin 5-$HT_6$ receptors in the brain is found in the tuberculum olfactorium, in the nucleus accumbens, in the striatum, in the gyrus dentatus and in the CA1-3 regions of the hippocampus. These regions are involved to a particularly great extent in psychiatric disorders, such as, for example, schizophrenia or depression. In addition, it is known from animal experiments that administration of 5-$HT_6$ antisense oligo-nucleotides causes a behaviour syndrome which corresponds to that of dopamine agonists. Furthermore, hyperactivity of the dopaminergic neurotransmitter system is pathophysiologically safeguarded in schizophrenia (dopamine hypothesis of schizophrenia). However, dysfunctions of the dopamine system have also been found in various clinical forms of depression. In addition, a large number of the established and also more recent therapeutic agents employed for the treatment of these psychiatric disorders in clinical practice bind to the 5-$HT_6$ receptor. Particular mention may be made here of atypical neuroleptics (for example clozapine) and the tricyclic antidepressants (for example amitriptyline).

In addition, it has been found in studies involving animal experiments that 5-$HT_6$ receptors in the brain control cholinergic neurotransmission. Cholinergics are employed in illnesses with memory disorders, such as, for example, Alzheimer's disease.

The efficacy of the compounds of the formula I as inhibitors of the 5-$HT_3$ receptor can be determined by the method of Richardson et al., Nature 1985, 316, 126 or by the method of Watling et al., European J. Pharmacol. 1988, 149, 397. Here, the compounds antagonise the action of serotonin at 5-HT$_3$ receptors, such as, for example, the serotonin-induced Bezold-Jarisch reflex (method, see J. Pharm. Pharmacol., 1980, 40, 301-302 and Nature 316, 126-131). In addition, these compounds displace the substance $^3$H-GR65630, which is known as a selective 5-HT$_3$ ligand, from the homogenised tissue from the endorhinal cortex of rats (see Europ. J. Pharmacol., 1989, 159, 157-164).

Illnesses which can be treated with the substances of the formula I thus include psychoses, schizophrenia, depression, anxiety states, dementia, in particular Alzheimer's disease and Lewy bodies dementia, neurodegenerative disorders, Parkinson's disease, amyotrophic lateral sclerosis, Huntington's disease, Tourette's syndrome, learning and memory restrictions, bulimia, anorexia nervosa or other eating disorders, compulsive behaviour, premenstrual syndrome, age-induced memory impairment, and amelioration of withdrawal symptoms in nicotine dependence. Owing to their neuroprotective action, compounds of the formula I are used in strokes and brain damage by toxic compounds. The compounds of the formula I and their physiologically acceptable salts are therefore suitable as therapeutic active ingredients for disorders of the central nervous system.

The compounds are suitable for the treatment of disorders which are characterised by an excess of circulating serotonin or by serotonergic hyperactivity. These include, in particular, psychoses, nausea and vomiting (occurring, for example, during chemotherapeutic or radiotherapeutic treatment of cancer diseases), irritable bowel syndrome, dementia or other cognitive disorders, migraine and addiction illnesses.

Compounds of the formula I and their salts and solvates are also suitable as intermediates for the preparation of other medicament active ingredients.

The invention relates to the compounds of the formula I and to their physiologically acceptable acid-addition salts. The invention also relates to the solvates, for example hydrates or alcoholates, of these compounds.

The term "solvates of the compounds of the formula I" is taken to mean adducts of inert solvent molecules onto the compounds of the formula I which form owing to their mutual attractive force. Solvates are, for example, monohydrates or dihydrates or addition compounds with alcohols, such as, for example, with methanol or ethanol.

Should radicals which have an asymmetrical carbon atom which can have different configurations be introduced via the radicals R$^1$ to R$^4$, for example 1-azabicyclo[2.2.2]oct-3-yl for R$^1$, the compounds of the formula I may exist in various optically active forms or alternatively as racemates or racemate mixtures.

The invention relates to the compounds of the formula I and their salts and solvates according to claim 1 and to a process for the preparation of compounds of the formula I and their salts and solvates, characterised in that a compound of the formula II

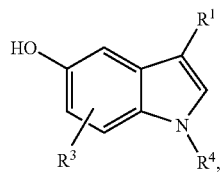

II in which R$^1$, R$^3$ and R$^4$ are as defined in claim 1, is reacted with a compound of the formula III

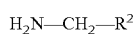

III, in which
R$^2$ is as defined in claim 1,
in the presence of an oxidant, and
if desired, the radical R$^1$=H is converted into another radical R$^1$ as defined in claim 1,
and/or
a base of the formula I obtained is converted into one of its salts by treatment with an acid.

The invention also relates to the compounds of the formula I according to claim 1 and their physiologically acceptable salts and solvates as medicament active ingredients.

The invention likewise relates to the compounds of the formula I according to claim 1 and their physiologically acceptable salts or solvates as ligands of the nicotinic acetylcholine receptor.

The invention likewise relates to the compounds of the formula I according to claim 1 and their physiologically acceptable salts or solvates as serotonergic ligands.

For all radicals which may occur more than once, such as, for example, A or Hal, their meanings are independent of one another.

A is linear or branched alkyl having from 1 to 10 carbon atoms and preferably has 1, 2, 3, 4, 5, 6, 7, 8, 9 or 10 carbon atoms. Alkyl having from 1 to 10 carbon atoms is preferably methyl, furthermore ethyl, n-propyl, isopropyl, n-butyl, sec-butyl or tert-butyl, furthermore also n-pentyl, 1-, 2- or 3-methylbutyl, n-hexyl, 1-, 2-, 3- or 4-methylpentyl, n-heptyl, 1-, 2-, 3- or 4-ethylpentyl, n-octyl, n-nonyl or n-decyl.

Alkyl is particularly preferably methyl, isopropyl, n-propyl or 1-ethylpentyl.

Ar is phenyl, naphthyl or biphenyl, each of which is unsubstituted or monosubstituted or polysubstituted by Hal, A, OR$^5$, N(R$^5$)$_2$, NO$_2$, CN, COOR$^5$, CON(R$^5$)$_2$, NR$^5$COR$^5$, NR$^5$CON(R$^5$)$_2$, NR$^5$SO$_2$A, COR$^5$, SO$_2$NR$^5$, SO$_2$NR$^5$ or S(O)$_m$A, where A has one of the meanings indicated above, and R$^5$ and m have one of the meanings indicated below.

Ar is preferably unsubstituted or substituted phenyl, naphthyl or biphenyl, specifically preferably phenyl, o-, m- or p-tolyl, o-, m- or p-ethylphenyl, o-, m- or p-propylphenyl, o-, m- or p-isopropylphenyl, o-, m- or p-tert-butyl-phenyl, o-, m- or p-trifluoromethylphenyl, o-, m- or p-aminophenyl, o-, m- or p-hydroxyphenyl, o-, m- or p-nitrophenyl, o-, m- or p-(trifluoromethoxy)phenyl, o-, m- or p-cyanophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-(difluoromethoxy)phenyl, o-, m- or p-(fluoromethoxy)phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-dimethoxyphenyl, 3-nitro-4-chlorophenyl, 2,3,4-, 2,3,5-, 2,3,6-, 2,4,6- or 3,4,5-trichlorophenyl, 2,4,6-tri-tert-butyl-phenyl, furthermore preferably 2-nitro-4-(trifluoromethyl)phenyl, 3,5-di(trifluoromethyl)phenyl, 2,5-dimethylphenyl, 2-hydroxy-3,5-dichlorophenyl, 2-fluoro-5- or 4-fluoro-3-(trifluoromethyl)phenyl, 4-chloro-2- or 4-chloro-3-(trifluoromethyl)-, 2-chloro-4- or 2-chloro-5-(trifluoromethyl)phenyl, 4-bromo-2- or 4-bromo-3-(trifluoromethyl)phenyl, p-iodophenyl, 2-nitro-4-methoxyphenyl, 2,5-dimethoxy-4-nitrophenyl, 2-methyl-5-nitrophenyl, 2,4-dimethoxy-3-nitrophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl or 2,4,6-triisopropylphenyl.

Ar is particularly preferably, i.e. —$(CH_2)_n$—Ar where n=0, phenyl or o-methoxyphenyl.

—$(CH_2)_n$—Ar is arylalkyl if Ar has one of the meanings indicated above and n is 1, 2, 3, 4, 5, 6, 7 or 8. —$(CH_2)_n$—Ar where n≠0 is preferably benzyl, phenylethyl, phenylpropyl, phenylbutyl, phenylpentyl, phenylhexyl, phenylheptyl, naphthylmethyl, naphthylethyl, naphthylpropyl or naphthylbutyl. —$(CH_2)_n$—Ar is particularly preferably benzyl or phenylethyl.

Cycloalkyl having from 3 to 10 carbon atoms is preferably cyclopropyl, cyclobutyl, cyclopentyl, cyclohexyl, cycloheptyl, cyclooctyl or 2,6,6-trimethyl-bicyclo[3.1.1]heptyl.

Cycloalkyl is likewise a monocyclic or bicyclic terpene, preferably p-menthane, menthol, pinane, bornane or camphor, including all known stereoisomeric forms, or adamantyl. For camphor, this is either L-camphor or D-camphor.

Cycloalkyl is particularly preferably 2,6,6-trimethylbicyclo[3.1.1]heptyl.

Hal is fluorine, chlorine, bromine or iodine, particularly preferably fluorine, chlorine or bromine.

Het is a saturated, unsaturated or aromatic monocyclic or bicyclic heterocyclic radical having from 5 to 10 ring members, which may contain from 1 to 4 N and/or from 1 to 4 S and/or from 1 to 4 O atoms and in which the heterocyclic radical may be monosubstituted, disubstituted or trisubstituted by Hal, A, —$[C(R^5)_2]_o$—Ar, —$[C(R^5)_2]_o$-cycloalkyl, $OR^5$, $N(R^5)_2$, $NO_2$, CN, $COOR^5$, $CON(R^5)_2$, $NR^5COA$, $NR^5CON(R^5)_2$, $NR^5SO_2A$, $COR^5$, $SO_2NR^5$ or $S(O)_mA$ and/or carbonyl oxygen, where A, Hal, Ar and cycloalkyl have one of the meanings indicated above, and $R^5$, o and m are as defined below.

Het is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, benzo-1,3-dioxol-5-yl, -6-yl, -7-yl or -4-yl, 2-, 4-, 5-, 6- or 7-benzothiazolyl, 4- or 5-benzothiadiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals may also be partially or fully hydrogenated. Het may thus also be 2,3-dihydro-2-, -3-, -4- or -5-furyl, 2,5-dihydro-2-, -3-, -4- or -5-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or -4-imidazolyl, 2,3-dihydro-1-, -2-, -3-, -4-, -5-, -6- or -7-1H-indolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or 4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl.

Het is particularly preferably 2- or 3-thienyl, imidazol-1-yl, pyridin-3-yl, benzothien-3-yl, 6-methoxy-1H-indol-3-yl, benzo-1,3-dioxol-5-yl, tetrahydrofuran-2-yl, morpholin-4-yl, 4-methylpiperazin-1-yl or 2-oxopyrrolidin-1-yl.

—$(CH_2)_n$-Het is particularly preferably pyridin-3-yl, thien-2-yl, benzo-1,3-dioxol-5-yl, tetrahydrofuran-2-yl, benzothien-3-yl, thien-3-ylmethyl, 6-methoxy-1H-indol-3-ylmethyl, morpholin-4-ylethyl, 2-oxopyrrolidin-1-ylethyl, (4-methyl)piperidin-1-ylethyl or imidazol-1-ylethyl.

$Het^1$ is a saturated, unsaturated or aromatic monocyclic, bicyclic or tricyclic heterocyclic radical having from 5 to 10 ring members which contains at least 1 N atom and in which the heterocyclic radical may be monosubstituted, disubstituted or trisubstituted by Hal, A, $OR^5$, $N(R^5)_2$, $NO_2$, CN and/or carbonyl oxygen, where A is as defined above, and $R^5$ is as defined below.

$Het^1$ is preferably substituted or unsubstituted 1-, 2- or 3-pyrrolyl, 1-, 2-, 4- or 5-imidazolyl, 3-, 4- or 5-pyrazolyl, 2-, 3- or 4-pyridyl, 2-, 4-, 5- or 6-pyrimidinyl, furthermore preferably 3- or 4-pyridazinyl, pyrazinyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 1-, 2-, 3-, 4-, 5-, 6-, 7- or 8-quinolinyl, 1-, 3-, 4-, 5-, 6-, 7- or 8-isoquinolinyl, 3-, 4-, 5-, 6-, 7- or 8-cinnolinyl, 1-, 4-, 5-, 6-, 7- or 8-phthalazinyl, 2-, 3-, 5-, 6-, 7- or 8-quinoxalinyl, 2-, 4-, 5-, 6-, 7- or 8-quinazolinyl. The heterocyclic radicals may also be partially or fully hydrogenated. $Het^1$ may thus also be 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or -4-imidazolyl, 2,3-dihydro-1-, -2-, -3-, -4-, -5-, -6- or -7-1H-indolyl, 2,3-dihydro-1-, -2-, -3-, -4- or -5-pyrazolyl, tetrahydro-1-, -3- or -4-pyrazolyl, 1,5-dihydroimidazol-4-on-2- or -5-yl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 1-, 2-, 3- or 4-azepanyl, tetrahydro-2-, -3- or -4-pyranyl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl or 1-azabicyclo[2.2.2]oct-3-yl. A synonym for 1-azabicyclo[2.2.2]oct-3-yl is quinuclidin-3-yl.

The said heterocyclic rings may also be monosubstituted or disubstituted by =O or $NHR^5$.

$Het^1$ is particularly preferably 1-azabicyclo[2.2.2]oct-3-yl, piperidin-3-yl, piperidin-4-yl or 1-methylpiperidin-4-yl.

$R^1$ is hydrogen or $Het^1$, where $Het^1$ is as defined above.

$R^1$ is preferably hydrogen, 1-azabicyclo[2.2.2]oct-3-yl, piperidin-3-yl, piperidin-4-yl or 1-methylpiperidin-4-yl.

$R^2$ is H, A, cycloalkyl, —$(CH_2)_p$—$N(R^5)_2$, —$(CH_2)_p$—$OR^5$, —$(CH_2)_n$—Ar or —$(CH_2)_n$-Het, where $R^5$ is as defined below, and n may be 0, 1, 2, 3, 4, 5, 6, 7 or 8 and p is 1, 2, 3, 4, 5, 6, 7 or 8. A, cycloalkyl, Ar and Het have the preferred and particularly preferred meanings indicated above.

n is preferably 0, 1 or 2.

p is preferably 1 or 2.

$R^2$ is preferably hydrogen, A, cycloalkyl, phenyl, o-methoxyphenyl, pyridin-3-yl, thien-2-yl, benzo-1,3-dioxol-5-yl, tetrahydrofuran-2-yl, benzothien-3-yl, methoxymethyl, thien-3-ylmethyl, 6-methoxy-1H-indol-3-ylmethyl, 2-dimethylaminoethyl, morpholin-4-ylethyl, 2-oxopyrrolidin-1-ylethyl, (4-methyl)piperidin-1-ylethyl or imidazol-1-ylethyl.

$R^3$ is H, Hal, OH, OA or O—$(CH_2)_n$—Ar, where Hal, A, Ar and n are as defined above.

$R^3$ is preferably hydrogen.

$R^4$ is H, A or O—$(CH_2)_n$—Ar, where A, Ar and n are as defined above.

$R^4$ is preferably hydrogen.

$R^5$ is H or A, where A is as defined above.

—$(CH_2)_p$—$OR^5$ is particularly preferably methoxymethyl.

—$(CH_2)_p$—$N(R^5)_2$ is particularly preferably 2-dimethylaminoethyl.

m is 1 or 2, where m is preferably 2.

o is 0, 1, 2, 3 or 4. o is preferably 0 or 1.

The invention accordingly relates, in particular, to the compounds of the formula I in which at least one of the said radicals has one of the preferred meanings indicated above. Some preferred groups of compounds may be expressed by the following sub-formulae Ia to Ij, which conform to the formula I and in which the radicals not designated in greater detail have the meaning indicated for the formula I, but in which in Ia $R^4$ is hydrogen;

in Ib $R^3$ is hydrogen;

in Ic $R^3$ is hydrogen and $R^4$ is hydrogen;

in Id $R^1$ is hydrogen;

in Ie $R^1$ is $Het^1$;

in If $R^1$ is hydrogen, 1-azabicyclo[2.2.2]oct-3-yl, piperidin-3-yl, piperidin-4-yl or 1-methylpiperidin-4-yl;

in Ig $R^1$ is hydrogen, $R^2$ is hydrogen, —$(CH_2)_n$-Het or —$(CH_2)_p$—$N(R^5)_2$, $R^3$ is hydrogen, $R^4$ is hydrogen and $R^5$ is A;

in Ih $R^1$ is 1-azabicyclo[2.2.2]oct-3-yl, $R^2$ is hydrogen, A, cycloalkyl, —$(CH_2)_n$—Ar, —$(CH_2)_p$—$OR^5$, —$(CH_2)_n$-Het or —$(CH_2)_p$—$N(R^5)_2$, $R^3$ is hydrogen, $R^4$ is hydrogen and $R^5$ is A;

in Ii $R^1$ is piperidin-4-yl or 1-methylpiperidin-4-yl, $R^2$ is hydrogen, A, —$(CH_2)_n$—Ar, —$(CH_2)_n$-Het or —$(CH_2)_p$—$N(R^5)_2$, $R^3$ is hydrogen, $R^4$ is hydrogen and $R^5$ is A;

in Ij $R^2$ is hydrogen, A, cycloalkyl, phenyl, o-methoxyphenyl, pyridin-3-yl, thien-2-yl, benzo-1,3-dioxol-5-yl, tetrahydrofuran-2-yl, benzothien-3-yl, methoxymethyl, thien-3-ylmethyl, 6-methoxy-1H-indol-3-ylmethyl, 2-dimethylaminoethyl, morpholin-4-yl-ethyl, 2-oxopyrrolidin-1-ylethyl, (4-methyl)piperidin-1-ylethyl or imidazol-1-ylethyl.

The invention relates, in particular, to the compounds according to claim 6 and their salts and solvates.

The compounds of the formula I and also the starting materials for their preparation are, in addition, prepared by methods known per se, as described in the literature (for example in the standard works, such as Houben-Weyl, Methoden der Organischen Chemie [Methods of Organic Chemistry], Georg Thieme Verlag, Stuttgart; Organic Reactions, John Wiley & Sons, Inc., New York), to be precise under reaction conditions as are known and suitable for the said reactions. Use can also be made here of variants which are known per se, but are not mentioned here in greater detail.

The starting materials for the claimed process can also be formed in situ by not isolating them from the reaction mixture, but instead immediately converting them further into the compounds of the formula I. On the other hand, it is possible to carry out the reaction in steps.

The compounds of the formula I can preferably be obtained by reacting compounds of the formula II, in which $R^1$, $R^3$ and $R^4$ are as defined in claim 1, with compounds of the formula III, in which $R^2$ is as defined in claim 1.

Compounds of the formula II and their preparation are disclosed in EP 450 345 (EP 450 345 B1: column 3, line 8, to column 4, line 38). EP 450 345 is hereby incorporated by way of reference.

The amines of the formula III are generally known or are commercially available; the compounds of the formula III which are not known can easily be prepared analogously to the known compounds.

The reaction of compounds of the formula II with amines of the formula III is carried out in the presence of an oxidant.

Suitable oxidants are manganese oxide ($MnO_2$), hydrogen peroxide ($H_2O_2$), ozone ($O_3$), potassium permanganate, chromium oxide, sodium chromate or potassium chromate.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, N-methylpyrrolidone (NMP), dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Depending on the conditions used, the reaction temperature is between about −10° and 150°, normally between 0° and 130°, preferably between 0° and 50°, particularly preferably room temperature.

Depending on the conditions used, the reaction time is between a few minutes and several days.

A base of the formula I obtained can be converted into the associated acid-addition salt using an acid. Suitable acids for this reaction are those which give physiologically acceptable salts. Thus, it is possible to use inorganic acids, for example sulfuric acid, hydrohalic acids, such as hydrochloric acid or hydrobromic acid, phosphoric acids, such as orthophosphoric acid, nitric acid, sulfamic acid, furthermore organic acids, specifically aliphatic, alicyclic, araliphatic, aromatic or heterocyclic monobasic or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalenemono- and -disulfonic acids and laurylsulfuric acid.

The free bases of the formula I can, if desired, be liberated from their salts by treatment with strong bases, such as sodium hydroxide, potassium hydroxide, sodium carbonate or potassium carbonate, so long as no further acidic groups are present in the molecule.

The invention furthermore relates to the medicament active ingredients according to the invention as nicotinic acetylcholine receptor ligands and/or serotonergic ligands for the prophylaxis or treatment of schizophrenia, depression, anxiety states, dementia, Alzheimer's disease, Lewy bodies dementia, neurodegenerative disorders, Parkinson's disease, Huntington's disease, Tourette's syndrome, learning and memory restrictions, age-induced memory impairment, amelioration of withdrawal symptoms in nicotine dependence, strokes or brain damage by toxic compounds.

The invention furthermore relates to pharmaceutical preparations comprising at least one compound of the formula I and/or one of its physiologically acceptable salts or solvates. The compounds of the formula I here can be converted into a suitable dosage form together with at least one solid, liquid and/or semi-liquid excipient or adjuvant and if desired in combination with one or more further active ingredients.

These preparations can be used as medicaments in human or veterinary medicine. Suitable excipients are organic or inorganic substances which are suitable for enteral (for example oral), parenteral or topical administration and which do not react with the novel compounds, for example water, vegetable oils, benzyl alcohols, alkylene glycols, polyethylene glycols, glycerol triacetate, gelatine, carbohydrates, such as lactose or starch, magnesium stearate, talc and Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The preparations indicated may be sterilised and/or comprise adjuvants, such as lubricants, preservatives, stabilisers and/or wetting agents, emulsifiers, salts for modifying the osmotic pressure, buffer substances, colorants, flavours and/or a plurality of further active ingredients, for example one or more vitamins.

The substances according to the invention are generally administered analogously to known, commercially available preparations (for example Tae-rin), preferably in doses of between about 5 mg and 100 mg, in particular between 10 and 40 mg per dosage unit. The daily dose is preferably between about 0.5 and 1 mg/kg of body weight.

The specific dose for each individual patient depends on a very wide variety of factors, for example on the efficacy of the specific compound employed, on the age, body weight, general state of health, sex, on the diet, on the time and method of administration, on the excretion rate, medicament combination and severity of the particular disorder to which the therapy applies.

Oral administration is preferred.

The above-mentioned compounds of the formula I are used for the preparation of medicaments, in particular medicaments which are employed for the treatment of disorders based on dysfunction of nicotinic acetylcholine receptors.

The invention likewise relates to the use of compounds of the formula I according to claim 1 and/or their physiologically acceptable salts or solvates for the preparation of a medicament, in particular for the preparation of a medicament for the treatment of disorders in which the binding to nicotinic acetylcholine receptors results in an improvement in the clinical picture.

The invention furthermore relates to the use of compounds of the formula I according to claim 1 and/or of their physiologically acceptable salts and solvates for the preparation of a medicament for the prophylaxis or treatment of psychoses, schizophrenia, depression, anxiety states, dementia, in particular Alzheimer's disease and Lewy bodies dementia, neurodegenerative disorders, Parkinson's disease, amyotrophic lateral sclerosis, Huntington's disease, Tourette's syndrome, learning and memory restrictions, bulimia, anorexia nervosa or other eating disorders, compulsive behaviour, premenstrual syndrome, age-induced memory impairment, amelioration of withdrawal symptoms in nicotine dependence, strokes or brain damage by toxic compounds.

The invention furthermore relates to the use of compounds of the formula I according to claim 1 and/or of their physiologically acceptable salts and solvates for the preparation of a medicament for the treatment of disorders that are characterised by an excess of circulating serotonin or by serotonergic hyperactivity, in particular of nausea or vomiting.

Even without further details, it is assumed that a person skilled in the art will be able to use the above description in the broadest scope. The preferred embodiments should therefore merely be regarded as descriptive disclosure which is absolutely not limiting in any way.

Above and below, all temperatures are given in ° C. In the following examples, "conventional work-up" means that, if necessary, the solvent is removed, water is added if necessary, the pH is, if necessary, adjusted to between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation. The purified compounds are, if desired, freeze-dried.

Mass spectrometry (MS): ESI (electrospray ionisation) $(M+H)^+$

EXAMPLE 1

0.5 mmol of methylamine and 4.13 mmol of $MnO_2$ are added to a solution of 0.4 mmol of 5-hydroxy-1H-indole in 3 ml of DMF, and the mixture is stirred at room temperature for 18 hours. The suspension is filtered through Celite and subjected to conventional work-up, giving 6H-oxazolo-[4,5-e]indole; ESI 159.

Reaction of the free base with 1N HCl solution in methanol gives 6H-oxazolo[4,5-e]indole hydrochloride.

EXAMPLE 2

Analogously to Example 1, reaction of 5-hydroxy-1H-indole with $N^1,N^1$-dimethylpropane-1,3-diamine gives dimethyl[2-(6H-oxazolo[4,5-e]indol-2-yl)ethyl]amine; ESI 230;

salt precipitation with 1N HCl solution gives dimethyl[2-(6H-oxazolo[4,5-e]indol-2-yl)ethyl]amine hydrochloride, 3-imidazol-1-ylpropylamine gives 2-(2-imidazol-1-yl-ethyl)-6H-oxazolo[4,5-e]indole; ESI 253;

salt precipitation with 1N HCl solution gives 2-(2-imidazol-1-ylethyl)-6H-oxazolo[4,5-e]indole hydrochloride, 3-(4-methylpiperazin-1-yl)propylamine gives 2-[2-(4-methylpiperazin-1-yl)ethyl]-6H-oxazolo[4,5-e]indole; ESI 285;

salt precipitation with 1N HCl solution gives 2-[2-(4-methylpiperazin-1-yl)ethyl]-6H-oxazolo[4,5-e]indole hydrochloride, 3-morpholin-4-ylpropylamine gives 2-(2-morpholin-4-yl-ethyl)-6H-oxazolo[4,5-e]indole; ESI 272;

salt precipitation with 1N HCl solution gives 2-(2-morpholin-4-ylethyl)-6H-oxazolo[4,5-e]indole hydrochloride, 1-(3-aminopropyl)pyrrolidin-2-one 1-[2-(6H-oxazolo[4,5-e]indol-2-yl)ethyl]pyrrolidin-2-one; ESI 270;

salt precipitation with 1N HCl solution gives 1-[2-(6H-oxazolo[4,5-e]indol-2-yl)ethyl]pyrrolidin-2-one hydrochloride, C-pyridin-3-ylmethylamine gives 2-pyridin-3-yl-6H-oxazolo[4,5-e]indole; ESI 236;

salt precipitation with 1N HCl solution gives 2-pyridin-3-yl-6H-oxazolo[4,5-e]indole hydrochloride;

2-(6-methoxy-1H-indol-3-yl)ethylamine gives 2-(6-methoxy-1H-indol-3-ylmethyl)-6H-oxazolo[4,5-e]indole; ESI 318;

salt precipitation with 1N HCl solution gives 2-(6-methoxy-1H-indol-3-ylmethyl)-6H-oxazolo[4,5-e]indole hydrochloride.

EXAMPLE 3

Analogously to Example 1, reaction of 3-(5-hydroxy-1H-indol-3-yl)-1-aza-bicyclo[2.2.2]octane with butylamine gives 8-(1-azabicyclo[2.2.2]oct-3-yl)-2-propyl-6H-oxazolo[4,5-e]indole; ESI 310;

salt precipitation with 1N HCl solution gives 8-(1-azabicyclo[2.2.2]oct-3-yl)-2-propyl-6H-oxazolo[4,5-e]indole hydrochloride;

benzylamine gives 8-(1-azabicyclo[2.2.2]oct-3-yl)-2-phenyl-6H-oxazolo[4,5-e]indole; ESI 344;

salt precipitation with 1N HCl solution gives 8-(1-azabicyclo[2.2.2]oct-3-yl)-2-phenyl-6H-oxazolo[4,5-e]indole hydrochloride;

3-morpholin-4-ylpropylamine gives 8-(1-azabicyclo[2.2.2]oct-3-yl)-2-(2-morpholin-4-ylethyl)-6H-oxazolo[4,5-e]-indole; ESI 381;

salt precipitation with 1N HCl solution gives 8-(1-azabicyclo[2.2.2]oct-3-yl)-2-(2-morpholin-4-ylethyl)-6H-oxazolo[4,5-e]-indole hydrochloride;

C-benzo[b]thiophen-3-ylmethylamine gives 8-(1-azabicyclo[2.2.2]oct-3-yl)-2-benzo[b]thiophen-3-yl-6H-oxazolo[4,5-e]-indole; ESI 401;

salt precipitation with 1N HCl solution gives 8-(1-azabicyclo[2.2.2]oct-3-yl)-2-benzo[b]thiophen-3-yl-6H-oxazolo[4,5-e]-indole hydrochloride;

2-(6-methoxy-1H-indole-3-yl)ethylamine gives 8-(1-azabicyclo[2.2.2]oct-3-yl)-2-(5-methoxy-1H-indol-3-ylmethyl)-6H-oxazolo[4,5-e]indole; ESI 428;

salt precipitation with 1N HCl solution gives 8-(1-azabicyclo[2.2.2]oct-3-yl)-2-(5-methoxy-1H-indol-3-ylmethyl)-6H-oxazolo[4,5-e]indole hydrochloride;

C-(tetrahydrofuran-3-yl)methylamine gives 8-(1-azabicyclo[2.2.2]oct-3-yl)-2-(tetrahydrofuran-2-yl)-6H-oxazolo[4,5-e]-indole; ESI 338;

salt precipitation with 1N HCl solution gives 8-(1-azabicyclo[2.2.2]oct-3-yl)-2-(tetrahydrofuran-2-yl)-6H-oxazolo[4,5-e]-indole hydrochloride;

3-(4-methylpiperazin-1-yl)propylamine gives 8-(1-azabicyclo[2.2.2]oct-3-yl)-2-[2-(4-methylpiperazin-1-yl)ethyl]-6H-oxazolo[4,5-e]indole; ESI 395;

salt precipitation with 1N HCl solution gives 8-(1-azabicyclo[2.2.2]oct-3-yl)-2-[2-(4-methylpiperazin-1-yl)ethyl]-6H-oxazolo[4,5-e]indole hydrochloride;

3-imidazol-1-ylpropylamine gives 8-(1-azabicyclo[2.2.2]oct-3-yl)-2-(2-imidazol-1-ylethyl)-6H-oxazolo[4,5-e]-indole; ESI 362;

salt precipitation with 1N HCl solution gives 8-(1-azabicyclo[2.2.2]oct-3-yl)-2-(2-imidazol-1-ylethyl)-6H-oxazolo[4,5-e]-indole hydrochloride;

2-ethylhexylamine gives 8-(1-azabicyclo[2.2.2]oct-3-yl)-2-(1-ethylpentyl)-6H-oxazolo[4,5-e]indole; ESI 367;

salt precipitation with 1N HCl solution gives 8-(1-azabicyclo[2.2.2]oct-3-yl)-2-(1-ethylpentyl)-6H-oxazolo[4,5-e]indole hydrochloride;

2-methoxybenzylamine gives 8-(1-azabicyclo[2.2.2]oct-3-yl)-2-(2-methoxyphenyl)-6H-oxazolo[4,5-e]-indole; ESI 374;

salt precipitation with 1N HCl solution gives 8-(1-azabicyclo[2.2.2]oct-3-yl)-2-(2-methoxyphenyl)-6H-oxazolo[4,5-e]-indole hydrochloride;

2-methoxyethylamine gives 8-(1-azabicyclo[2.2.2]oct-3-yl)-2-methoxymethyl-6H-oxazolo[4,5-e]indole; ESI 312;

salt precipitation with 1N HCl solution gives 8-(1-azabicyclo[2.2.2]oct-3-yl)-2-methoxymethyl-6H-oxazolo[4,5-e]indole hydrochloride;

ethylamine gives 8-(1-azabicyclo[2.2.2]oct-3-yl)-2-methyl-6H-oxazolo[4,5-e]indole; ESI 282;

salt precipitation with 1N HCl solution gives 8-(1-azabicyclo[2.2.2]oct-3-yl)-2-methyl-6H-oxazolo[4,5-e]indole hydrochloride;

Isobutylamine gives 8-(1-azabicyclo[2.2.2]oct-3-yl)-2-isopropyl-6H-oxazolo[4,5-e]indole; ESI 310;

salt precipitation with 1N HCl solution gives 8-(1-azabicyclo[2.2.2]oct-3-yl)-2-isopropyl-6H-oxazolo[4,5-e]indole hydrochloride;

C-benzo-1,3-dioxol-5-ylmethylamine gives 8-(1-azabicyclo[2.2.2]oct-3-yl)-2-benzo-1,3-dioxol-5-yl-6H-oxazolo[4,5-e]-indole; ESI 388;

salt precipitation with 1N HCl solution gives 8-(1-azabicyclo[2.2.2]oct-3-yl)-2-benzo-1,3-dioxol-5-yl-6H-oxazolo[4,5-e]-indole hydrochloride;

1-(3-aminopropyl)pyrrolidin-2-one gives 1-{2-[8-(1-azabicyclo[2.2.2]oct-3-yl)-6H-oxazolo[4,5-e]indol-2-yl]ethyl}-pyrrolidin-2-one; ESI 379;

salt precipitation with 1N HCl solution gives 1-{2-[8-(1-azabicyclo[2.2.2]oct-3-yl)-6H-oxazolo[4,5-e]indol-2-yl]ethyl}-pyrrolidin-2-one hydrochloride;

C-(2,6,6-trimethylbicyclo[3.1.1]hept-3-yl)methylamine gives 8-(1-azabicyclo[2.2.2]oct-3-yl)-2-(2,6,6-trimethylbicyclo[3.1.1]hept-3-yl)-6H-oxazolo[4,5-e]indole; ESI 405;

salt precipitation with 1N HCl solution gives 8-(1-azabicyclo[2.2.2]oct-3-yl)-2-(2,6,6-trimethylbicyclo[3.1.1]hept-3-yl)-6H-oxazolo[4,5-e]indole hydrochloride;
methylamine gives 8-(1-azabicyclo[2.2.2]oct-3-yl)-6H-oxazolo[4,5-e]indole; ESI 268;

salt precipitation with 1N HCl solution gives 8-(1-azabicyclo[2.2.2]oct-3-yl)-6H-oxazolo[4,5-e]indole hydrochloride;
2-thiophen-2-ylethylamine gives 8-(1-azabicyclo[2.2.2]oct-3-yl)-2-thiophen-2-ylmethyl-6H-oxazolo[4,5-e]-indole; ESI 364;

salt precipitation with 1N HCl solution gives 8-(1-azabicyclo[2.2.2]oct-3-yl)-2-thiophen-2-ylmethyl-6H-oxazolo[4,5-e]-indole hydrochloride;
C-pyridin-3-ylmethylamine gives 8-(1-azabicyclo[2.2.2]oct-3-yl)-2-pyridin-3-yl-6H-oxazolo[4,5-e]indole; ESI 345;

salt precipitation with 1N HCl solution gives 8-(1-azabicyclo[2.2.2]oct-3-yl)-2-pyridin-3-yl-6H-oxazolo[4,5-e]indole hydrochloride;
$N^1,N^1$-dimethylpropane-1,3-diamine gives {2-[8-(1-azabicyclo[2.2.2]oct-3-yl)-6H-oxazolo[4,5-e]indol-2-yl]ethyl}-dimethylamine; ESI 339;

salt precipitation with 1N HCl solution gives {2-[8-(1-azabicyclo[2.2.2]oct-3-yl)-6H-oxazolo[4,5-e]indol-2-yl]ethyl}-dimethylamine hydrochloride;
2-(6-methoxy-1H-indol-3-yl)ethylamine gives 8-(1-azabicyclo[2.2.2]oct-3-yl)-2-(6-methoxy-1H-indol-3-ylmethyl)-6H-oxazolo[4,5-e]indole; ESI 428;

salt precipitation with 1N HCl solution gives 8-(1-azabicyclo[2.2.2]oct-3-yl)-2-(6-methoxy-1H-indol-3-ylmethyl)-6H-oxazolo[4,5-e]indole hydrochloride.

EXAMPLE 4

Analogously to Example 1, reaction of 3-(1-methylpiperidin-4-yl)-1H-indol-5-ol with
butylamine gives 8-(1-methylpiperidin-4-yl)-2-propyl-6H-oxazolo[4,5-e]indole; ESI 298;

salt precipitation with 1N HCl solution gives 8-(1-methylpiperidin-4-yl)-2-propyl-6H-oxazolo[4,5-e]indole hydrochloride;
benzylamine gives 8-(1-methylpiperidin-4-yl)-2-phenyl-6H-oxazolo[4,5-e]indole; ESI 332;

salt precipitation with 1N HCl solution gives 8-(1-methylpiperidin-4-yl)-2-phenyl-6H-oxazolo[4,5-e]indole hydrochloride;
2-thiophen-2-ylethylamine gives 8-(1-methylpiperidin-4-yl)-2-thiophen-2-ylmethyl-6H-oxazolo[4,5-e]indole; ESI 352;

salt precipitation with 1N HCl solution gives 8-(1-methylpiperidin-4-yl)-2-thiophen-2-ylmethyl-6H-oxazolo[4,5-e]indole hydrochloride;
$N^1,N^1$-dimethylpropane-1,3-diamine gives dimethyl{2-[8-(1-methylpiperidin-4-yl)-6H-oxazolo[4,5-e]indol-2-yl]ethyl}-amine; ESI 327;

salt precipitation with 1N HCl solution gives dimethyl{2-[8-(1-methylpiperidin-4-yl)-6H-oxazolo[4,5-e]indol-2-yl]ethyl}-amine hydrochloride;
2-(6-methoxy-1H-indol-3-yl)ethylamine gives 2-(6-methoxy-1H-indol-3-ylmethyl)-8-(1-methylpiperidin-4-yl)-6H-oxazolo-[4,5-e]indole; ESI 416;

salt precipitation with 1N HCl solution gives 2-(6-methoxy-1H-indol-3-ylmethyl)-8-(1-methylpiperidin-4-yl)-6H-oxazolo-[4,5-e]indole hydrochloride;
C-benzo[b]thiophen-3-ylmethylamine gives 2-benzo[b]thiophen-3-yl-8-(1-methylpiperidin-4-yl)-6H-oxazolo[4,5-e]indole; ESI 389;

salt precipitation with 1N HCl solution gives 2-benzo[b]thiophen-3-yl-8-(1-methylpiperidin-4-yl)-6H-oxazolo[4,5-e]indole hydrochloride;
methylamine gives 8-(1-methylpiperidin-4-yl)-6H-oxazolo[4,5-e]indole; ESI 256;

salt precipitation with 1N HCl solution gives 8-(1-methylpiperidin-4-yl)-6H-oxazolo[4,5-e]indole hydrochloride;
1-(3-aminopropyl)pyrrolidin-2-one 1-{2-8-(1-methylpiperidin-4-yl)-6H-oxazolo[4,5-e]indol-2-yl]ethyl}pyrrolidin-2-one; ESI 367;

salt precipitation with 1N HCl solution gives 1-{2-8-(1-methylpiperidin-4-yl)-6H-oxazolo[4,5-e]indol-2-yl]ethyl}pyrrolidin-2-one hydrochloride;
3-morpholin-4-ylpropylamine gives 8-(1-methylpiperidin-4-yl)-2-(2-morpholin-4-ylethyl)-6H-oxazolo[4,5-e]indole; ESI 369;

salt precipitation with 1N HCl solution gives 8-(1-methylpiperidin-4-yl)-2-(2-morpholin-4-ylethyl)-6H-oxazolo[4,5-e]indole hydrochloride;
3-(4-methylpiperazin-1-yl)propylamine gives 2-[2-(4-methylpiperazin-1-yl)ethyl]-8-(1-methylpiperidin-4-yl)-6H-oxazolo-[4,5-e]indole; ESI 383;

salt precipitation with 1N HCl solution gives 2-[2-(4-methylpiperazin-1-yl)ethyl]-8-(1-methylpiperidin-4-yl)-6H-oxazolo-[4,5-e]indole hydrochloride;
3-imidazol-1-ylpropylamine gives 2-(2-imidazol-1-ylethyl)-8-(1-methylpiperidin-4-yl)-6H-oxazolo[4,5-e]indole; ESI 350;

salt precipitation with 1N HCl solution gives 2-(2-imidazol-1-ylethyl)-8-(1-methylpiperidin-4-yl)-6H-oxazolo[4,5-e]indole hydrochloride;
pyridin-3-ylmethylamine gives 8-(1-methylpiperidin-4-yl)-2-pyridin-3-yl-6H-oxazolo[4,5-e]indole; ESI 333;

salt precipitation with 1N HCl solution gives 8-(1-methylpiperidin-4-yl)-2-pyridin-3-yl-6H-oxazolo[4,5-e]indole hydrochloride.

EXAMPLE 5

Analogously to Example 1, reaction of 3-piperidin-4-yl-1H-indol-5-ol with
2-thiophen-3-ylethylamine gives 8-piperidin-4-yl-2-thiophen-3-ylmethyl-6H-oxazolo[4,5-e]indole; ESI 338;

salt precipitation with 1N HCl solution gives 8-piperidin-4-yl-2-thiophen-3-ylmethyl-6H-oxazolo[4,5-e]indole hydrochloride;
2-thiophen-2-ylethylamine gives 8-piperidin-4-yl-2-thiophen-2-ylmethyl-6H-oxazolo[4,5-e]indole; ESI 338;

salt precipitation with 1N HCl solution gives 8-piperidin-4-yl-2-thiophen-2-ylmethyl-6H-oxazolo[4,5-e]indole hydrochloride;

pyridin-3-ylmethylamine gives 8-piperidin-4-yl-2-pyridin-3-yl-6H-oxazolo[4,5-e]indole; ESI 319;

salt precipitation with 1N HCl solution gives 8-piperidin-4-yl-2-pyridin-3-yl-6H-oxazolo[4,5-e]indole hydrochloride;
$N^1,N^1$-dimethylpropane-1,3-diamine gives dimethyl[2-(8-piperidin-4-yl-6H-oxazolo[4,5-e]indol-2-yl)ethyl]amine; ESI 313;

salt precipitation with 1N HCl solution gives dimethyl[2-(8-piperidin-4-yl-6H-oxazolo[4,5-e]indol-2-yl)ethyl]amine hydrochloride;
2-(6-methoxy-1H-indol-3-yl)ethylamine gives 2-(6-methoxy-1H-indol-3-ylmethyl)-8-piperidin-4-yl-6H-oxazolo[4,5-e]indole; ESI 401;

salt precipitation with 1N HCl solution gives 2-(6-methoxy-1H-indol-3-ylmethyl)-8-piperidin-4-yl-6H-oxazolo[4,5-e]indole hydrochloride;
C-benzo[b]thiophen-3-ylmethylamine gives 2-benzo[b]thiophen-3-yl-8-piperidin-4-yl-6H-oxazolo[4,5-e]indole; ESI 374;

salt precipitation with 1N HCl solution gives 2-benzo[b]thiophen-3-yl-8-piperidin-4-yl-6H-oxazolo[4,5-e]indole hydrochloride;
1-(3-aminopropyl)pyrrolidin-2-one 1-[2-(8-piperidin-4-yl-6H-oxazolo[4,5-e]indol-2-yl)ethyl]pyrrolidin-2-one; ESI 353;

salt precipitation with 1N HCl solution gives 1-[2-(8-piperidin-4-yl-6H-oxazolo[4,5-e]indol-2-yl)ethyl]pyrrolidin-2-one hydrochloride;
3-morpholin-4-ylpropylamine gives 2-(2-morpholin-4-ylethyl)-8-piperidin-4-yl-6H-oxazolo[4,5-e]indole; ESI 355;

salt precipitation with 1N HCl solution gives 2-(2-morpholin-4-ylethyl)-8-piperidin-4-yl-6H-oxazolo[4,5-e]indole hydrochloride;
3-(4-methylpiperazin-1-yl)propylamine gives 2-[2-(4-methylpiperazin-1-yl)ethyl]-8-piperidin-4-yl-6H-oxazolo[4,5-e]indole; ESI 368;

salt precipitation with 1N HCl solution gives 2-[2-(4-methylpiperazin-1-yl)ethyl]-8-piperidin-4-yl-6H-oxazolo[4,5-e]indole hydrochloride;
3-imidazol-1-ylpropylamine gives 2-(2-imidazol-1-yl-ethyl)-8-piperidin-4-yl-6H-oxazolo[4,5-e]indole; ESI 336;

salt precipitation with 1N HCl solution gives 2-(2-imidazol-1-ylethyl)-8-piperidin-4-yl-6H-oxazolo[4,5-e]indole hydrochloride;
methylamine gives 8-piperidin-4-yl-6H-oxazolo[4,5-e]indole; ESI 242;

salt precipitation with 1N HCl solution gives 8-piperidin-4-yl-6H-oxazolo[4,5-e]indole hydrochloride.

EXAMPLE 6

Analogously to Example 1, reaction of 3-piperidin-3-yl-1H-indol-5-ol with
butylamine gives 8-piperidin-3-yl-2-propyl-6H-oxazolo[4,5-e]indole; ESI 284;

salt precipitation with 1N HCl solution gives 8-piperidin-3-yl-2-propyl-6H-oxazolo[4,5-e]indole hydrochloride.

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \times 2\ H_2O$, 28.48 g of $Na_2HPO_4 \times 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. Compounds of the general formula I

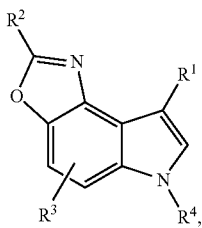

in which
$R^1$ is H or $Het^1$,
$R^2$ is H, A, cycloalkyl, o-methoxyphenyl, pyridin-3-yl, thien-2-yl, benzo-1,3-dioxol-5-yl, tetrahydrofuran-2-yl, benzothien-3-yl, methoxymethyl, thien-3-ylmethyl, 6-methoxy-1H-indol-3-ylmethyl, 2-dimethylaminoethyl, morpholin-4-ylethyl, 2-oxopyrrolidin-1-ylethyl, (4-methyl)piperidin-1-ylethyl or imidazol-1-ylethyl,
$R^3$ is H, Hal, OH, OA or O—$(CH_2)_n$—Ar,
$R^4$ is H, A or —$(CH_2)_n$—Ar,
$R^5$ is H or A,
A is a linear or branched alkyl group having from 1 to 10 carbon atoms,
Ar is phenyl, naphthyl or biphenyl, each of which is unsubstituted or monosubstituted or polysubstituted by Hal, A, $OR^5$, $N(R^5)_2$, $NO_2$, CN, $COOR^5$, $CON(R^5)_2$, $NR^5COR^5$, $NR^5CON(R^5)_2$, $NR^5SO_2A$, $COR^5$, $SO_2NR^5$ or $S(O)_mA$,
cycloalkyl is cycloalkyl having from 3 to 10 carbon atoms,
Hal is F, Cl, Br or I,
Het is a saturated, unsaturated or aromatic monocyclic or bicyclic heterocyclic radical having from 5 to 10 ring members, which may contain from 1 to 4 N and/or from 1 to 4 S and/or from 1 to 4 O atoms, and in which the heterocyclic radical may be monosubstituted, disubstituted or trisubstituted by Hal, A, —$[C(R^5)_2]_o$—Ar, —$[C(R^5)_2]_o$—cycloalkyl, $OR^5$, $N(R^5)_2$, $NO_2$, CN, $COOR^5$, $CON(R^5)_2$, $NR^5COA$, $NR^5CON(R^5)_2$, $NR^5SO_2A$, $COR^5$, $SO_2NR^5$ or $S(O)_mA$ and/or carbonyl oxygen,
$Het^1$ is a saturated, unsaturated or aromatic monocyclic, bicyclic or tricyclic heterocyclic radical having from 5 to 10 ring members which contains at least 1 N atom and in which the heterocyclic radical may be monosubstituted, disubstituted or trisubstituted by Hal, A, $OR^5$, $N(R^5)_2$, $NO_2$, CN and/or carbonyl oxygen,
n is 0, 1, 2, 3, 4, 5, 6, 7 or 8,
m is 1 or 2,
o is 0, 1, 2, 3 or 4,
p is 1, 2, 3, 4, 5, 6, 7 or 8,
and their physiologically acceptable salts and solvates.

2. Compounds of the formula I according to claim 1, in which $R^4$ is hydrogen.

3. Compounds of the formula I according to claim 1, in which $R^3$ is hydrogen.

4. Compounds of the formula I according to claim 1, in which $R^1$ is hydrogen, 1-azabicyclo[2.2.2]oct-3-yl, piperidin-3-yl, piperidin-4-yl or 1-methylpiperidin-4-yl.

5. Compounds of the formula I according to claim 1
   b) 8-(1-methylpiperidin-4-yl)-2-propyl-6H-oxazolo[4,5-e]indole;
   c) 8-piperidin-4-yl-2-thiophen-2-ylmethyl-6H-oxazolo[4,5-e]indole;
   d) 8-(1-azabicyclo[2.2.2]oct-3-yl)-2-thiophen-2-ylmethyl-6H-oxazolo[4,5-e]indole;
   e) 8-(1-azabicyclo[2.2.2]oct-3-yl)-2-(2-imidazol-1-ylethyl)-6H-oxazolo[4,5-e]indole;
   f) 2-[2-(4-methylpiperazin-1-yl)ethyl]-6H-oxazolo[4,5-e]indole or their physiologically acceptable salts or solvates.

6. Process for the preparation of compounds of the formula I according to claim 1, characterised in that a compound of the formula II

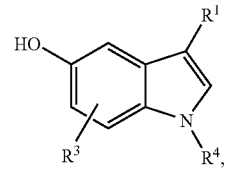

in which $R^1$, $R^3$ and $R^4$ are as defined in claim 1, is reacted with a compound of the formula III $$H_2N—CH_2—R^2 \quad III,$$

in which
$R^2$ is as defined in claim 1, in the presence of an oxidant, and if desired, the radical $R^1$=H is convened into another radical $R^1$, as defined in claim 1, and/or
a base of the formula I obtained is convened into one of its salts by treatment with an acid.

7. pharmaceutical composition, comprising at least one compound of the formula I according to claim 1 and/or a physiologically acceptable salt or solvates thereof, and a pharmaceutically acceptable carrier.

* * * * *

UNITED STATES PATENT AND TRADEMARK OFFICE
CERTIFICATE OF CORRECTION

PATENT NO. : 7,291,633 B2  Page 1 of 1
APPLICATION NO. : 10/476306
DATED : November 6, 2007
INVENTOR(S) : Henning Boettcher It is certified that error appears in the above-identified patent and that said Letters Patent is hereby corrected as shown below:

Column 17, line 41, reads "$SO^2NR^5$" should read -- $SO_2NR^5$ --

Column 18, line 27, begin new line after "indole"

Column 18, line 50, reads "is convened" should read -- is converted --

Column 18, line 52, reads "pharmaceutical" should read -- A pharmaceutical --

Signed and Sealed this

Third Day of February, 2009

JOHN DOLL
*Acting Director of the United States Patent and Trademark Office*